(12) United States Patent
Nakamura et al.

(10) Patent No.: US 9,304,193 B2
(45) Date of Patent: Apr. 5, 2016

(54) ULTRASOUND DIAGNOSTIC APPARATUS AND ULTRASOUND IMAGE PRODUCING METHOD

(75) Inventors: Kenji Nakamura, Kanagawa (JP); Hiroshi Murakami, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 122 days.

(21) Appl. No.: 13/338,983

(22) Filed: Dec. 28, 2011

(65) Prior Publication Data
US 2012/0197127 A1 Aug. 2, 2012

(30) Foreign Application Priority Data

Feb. 1, 2011 (JP) ................................. 2011-019630

(51) Int. Cl.
*A61B 8/14* (2006.01)
*G01S 7/52* (2006.01)
*G01S 15/89* (2006.01)
*A61B 8/00* (2006.01)
*G01S 7/00* (2006.01)

(52) U.S. Cl.
CPC ........... *G01S 7/52096* (2013.01); *G01S 7/5208* (2013.01); *G01S 7/52025* (2013.01); *G01S 15/8915* (2013.01); *A61B 8/14* (2013.01); *A61B 8/4472* (2013.01); *A61B 8/4483* (2013.01); *A61B 8/54* (2013.01); *G01S 7/003* (2013.01)

(58) Field of Classification Search
None
See application file for complete search history.

(56) References Cited

U.S. PATENT DOCUMENTS

| 5,329,930 | A | * | 7/1994 | Thomas et al. | 600/447 |
|---|---|---|---|---|---|
| 5,469,851 | A | * | 11/1995 | Lipschutz | 600/447 |
| 5,902,242 | A | * | 5/1999 | Ustuner et al. | 600/443 |
| 5,993,390 | A | * | 11/1999 | Savord et al. | 600/437 |
| 6,045,506 | A | * | 4/2000 | Hossack | 600/443 |
| 7,285,094 | B2 | * | 10/2007 | Nohara et al. | 600/447 |
| 7,443,765 | B2 | | 10/2008 | Thomenius et al. | |
| 7,508,737 | B1 | * | 3/2009 | Alexandru | 367/103 |

(Continued)

FOREIGN PATENT DOCUMENTS

| CN | 1794479 | 6/2006 |
|---|---|---|
| CN | 101858972 | 10/2010 |

(Continued)

OTHER PUBLICATIONS

JP Office Action dated Dec. 18, 2012, with partial English Translation; Application No. 2011-019630.

(Continued)

*Primary Examiner* — Long V Le
*Assistant Examiner* — Bradley Impink
(74) *Attorney, Agent, or Firm* — Young & Thompson

(57) ABSTRACT

An ultrasound diagnostic apparatus comprises a transducer array for transmitting ultrasonic beams to a subject, a multiplexer for sequentially selecting one channel of reception signal in every N number of channels of reception signals out of a plurality of channels of reception signals outputted from the transducer array which has received receiving ultrasonic echoes from the subject, a plurality of reception signal processors for sequentially processing an N number of channels of reception signals selected by the multiplexer to produce reception data, a beam former for performing beam forming on reception data sequentially produced by the plurality of reception signal processors and having time difference to produce sound ray signals, and an image producing unit for producing an ultrasound image based on the sound ray signals produced by the beam former.

16 Claims, 5 Drawing Sheets

(56) References Cited

U.S. PATENT DOCUMENTS

2004/0019277 A1* 1/2004 Bae .............................. 600/437
2005/0237858 A1 10/2005 Thomenius et al.
2011/0237950 A1 9/2011 Meng
2011/0299630 A1* 12/2011 Petrovic ........................ 375/340

FOREIGN PATENT DOCUMENTS

JP 2000-139912 5/2000
JP 2004-049926 2/2004

OTHER PUBLICATIONS

Chinese Office Action dated Aug. 20, 2014 in corresponding Chinese Patent Application No. 201210024938.8 with English translation of Chinese Office Action.

* cited by examiner

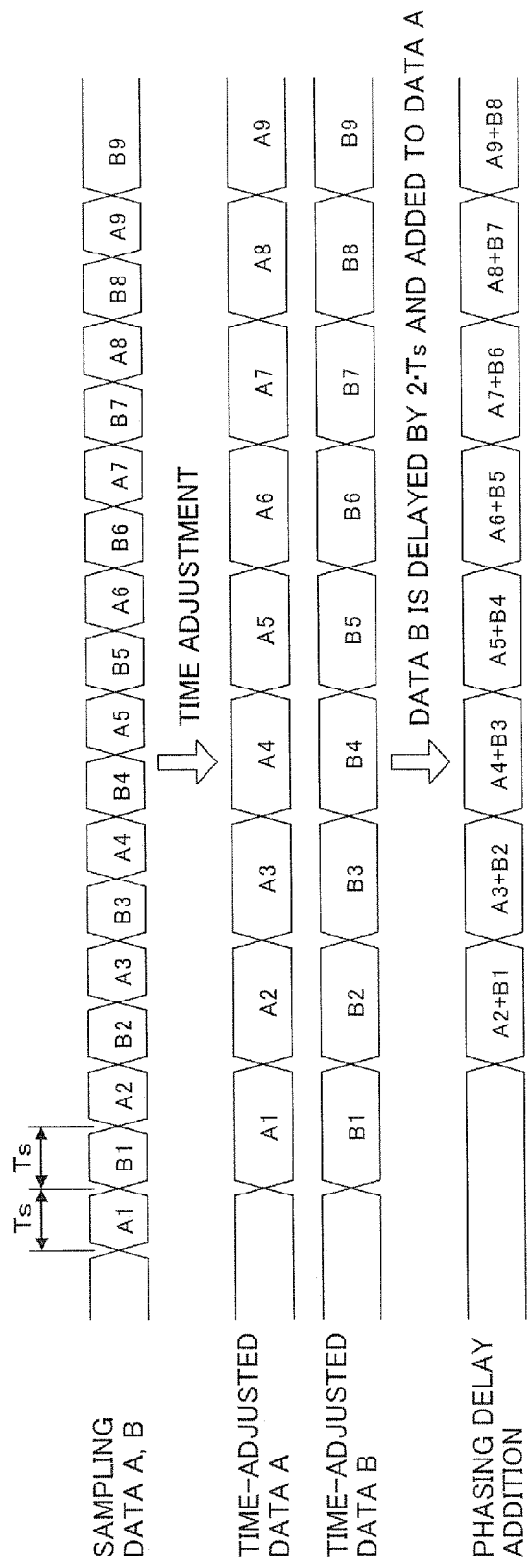

ULTRASOUND DIAGNOSTIC APPARATUS AND ULTRASOUND IMAGE PRODUCING METHOD

BACKGROUND OF THE INVENTION

The present invention relates to an ultrasound diagnostic apparatus and an ultrasound image producing method and particularly to reduction in electric power consumption by an ultrasound diagnostic apparatus for giving a diagnosis based on an ultrasound image produced by transmission and reception of ultrasonic waves from a transducer array of an ultrasound probe.

Conventionally, ultrasound diagnostic apparatus using ultrasound images are employed in the medical field. In general, this type of ultrasound diagnostic apparatus includes an ultrasound probe equipped with a built-in transducer array and an apparatus body connected to the ultrasound probe. The ultrasound probe transmits ultrasonic waves toward a subject and receives ultrasonic echoes from the subject. The received signals are then electrically processed in the apparatus body to generate an ultrasound image.

In recent years, there have been developed portable ultrasound diagnostic apparatus that can be brought to a bed or transported to a site for emergency medical care. This type of ultrasound diagnostic apparatus uses a battery for power supply, and, therefore, the power consumption of the apparatus greatly affects the time length of continuous use thereof. Since the amount of heat generated inside the apparatus increases with the power consumption, the dimensions of the apparatus needs to be increased as a measure to release heat, reducing the benefit of portability.

In particular, in a wireless probe connected wirelessly to the apparatus body, since transmission and reception circuits for transmitting ultrasonic waves from the transducers and receiving ultrasound echoes need to be housed in a compact probe, a great reduction in power consumption is demanded in these circuits.

Reduction in the number of mounted transmission and reception circuits would accordingly save on power consumption but when the number of simultaneous apertures also decreases with the number of transmission and reception circuits, high quality images are no longer to be obtained.

JP 2000-139912 A describes an ultrasound diagnostic apparatus wherein, in order to enable signal reception with broad apertures even when small-angle deflection is effected, the signals from a plurality of adjacent transducers are unequally added up to reduce the number of reception signals, followed by digital conversion and phasing delay addition by a beam former.

SUMMARY OF THE INVENTION

However, the apparatus described in JP 2000-139912 A still requires signal processors in a number corresponding to the reduced number of the reception signals, making it difficult to save on power consumption in the probe.

An object of the present invention is to provide an ultrasound diagnostic apparatus and an ultrasound image producing method that enable saving on power consumption while obtaining high quality images.

An ultrasound diagnostic apparatus according to the present invention comprises:

a transducer array for transmitting ultrasonic beams to a subject and receiving ultrasonic echoes from the subject;

a multiplexer for sequentially selecting one channel of reception signal in every N number of channels of reception signals out of a plurality of channels of reception signals outputted from the transducer array which has received receiving ultrasonic echoes from the subject;

a plurality of reception signal processors for sequentially processing an N number of channels of reception signals selected by the multiplexer to produce reception data;

a beam former for performing beam forming on reception data sequentially produced by the plurality of reception signal processors and having time difference to produce sound ray signals; and an image producing unit for producing an ultrasound image based on the sound ray signals produced by the beam former.

An ultrasound diagnostic method according to the present invention comprises the steps of:

transmitting an ultrasonic beam from an transducer array to a subject;

sequentially selecting one channel of reception signal in every N number of channels of reception signals out of a plurality of channels of reception signals outputted from the transducer array which has received receiving ultrasonic echoes from the subject;

producing reception data by sequentially processing a selected N number of channels of reception signals;

beam forming reception data sequentially produced and having time difference to produce sound ray signals; and producing an ultrasound image based on the produced sound ray signals.

BRIEF DESCRIPTION OF THE DRAWINGS

FIG. 5 is a timing chart illustrating how signal processing is performed in Embodiment 3.

DETAILED DESCRIPTION OF THE INVENTION

Embodiments of the present invention will be described below based on the appended drawings.

Embodiment 1

Figure 1:
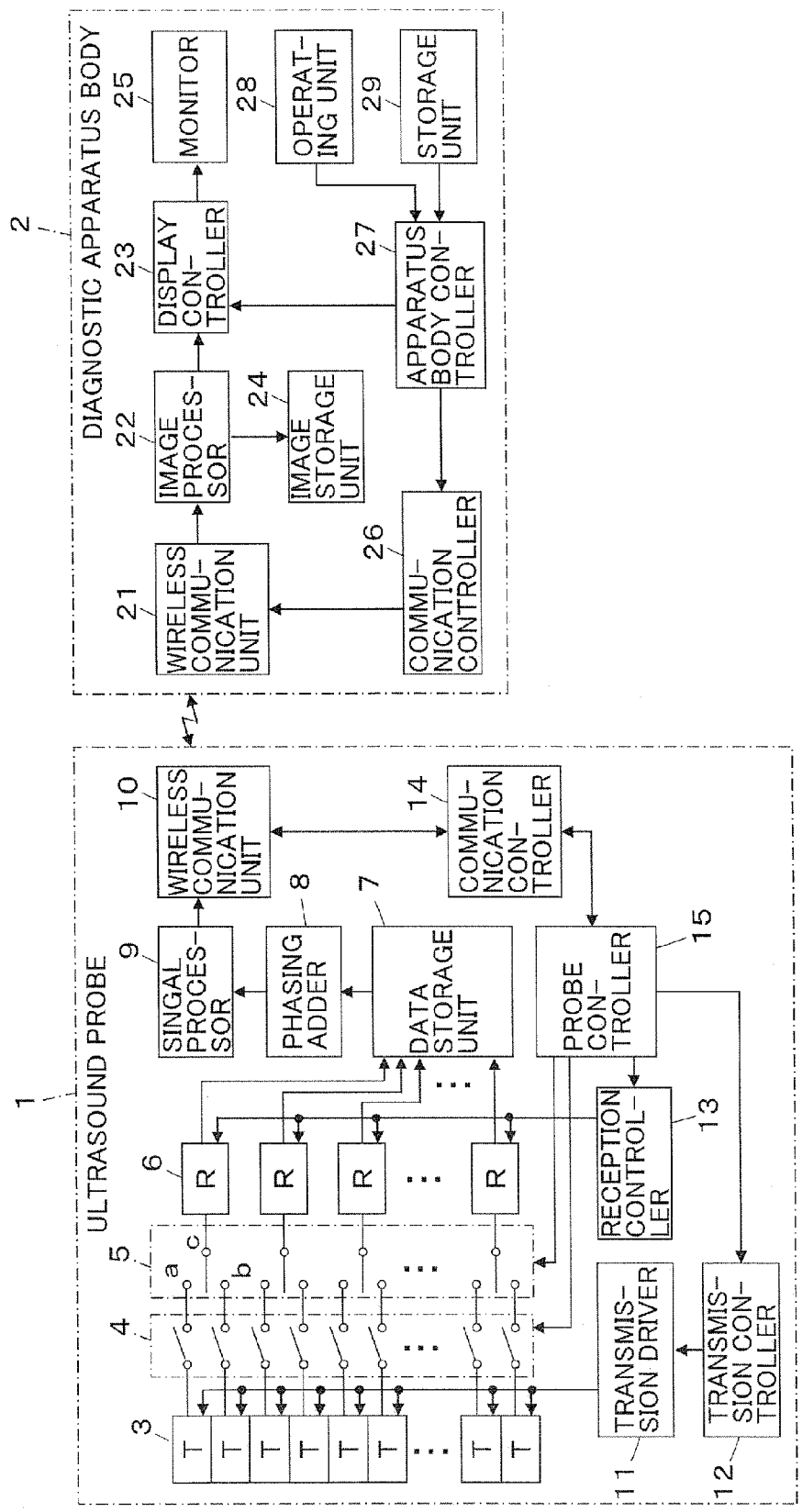
FIG. 1 is a block diagram illustrating a configuration of an ultrasound diagnostic apparatus according to Embodiment 1 of the invention.

FIG. 1 illustrates a configuration of an ultrasound diagnostic apparatus according to Embodiment 1 of the invention. The ultrasound diagnostic apparatus comprises an ultrasound probe 1 and a diagnostic apparatus body 2 that is connected to the ultrasound probe 1 via wireless communication.

The ultrasound probe 1 includes a plurality of ultrasound transducers 3 constituting a plurality of channels of a one-dimensional or two-dimensional transducer array, and a plurality of reception signal processors 6 is connected to the transducers 3 via a reception signal connecting section 4 and a multiplexer 5. A data storage unit 7 is connected to the reception signal processors 6, and a wireless communication unit 10 is connected to the data storage unit 7 via a phasing adder 8 and a signal processor 9 in sequence. Also, a transmission controller 12 is connected to the transducers 3 via a transmission driver 11, a reception controller 13 is connected to the reception signal processors 6, and a communication controller 14 is connected to the wireless communication unit 10. Further, a probe controller 15 is connected to the transmission controller 12, the reception controller 13, and the communication controller 14.

The transducers 3 each transmit ultrasonic waves according to driving signals supplied from the transmission driver 11 and receive ultrasonic echoes from the subject to output reception signals. Each of the transducers 3 is composed of an oscillator including, for example, a piezoelectric body made of a piezoelectric ceramic typified by PZT (lead zirconate titanate) or a piezoelectric polymer typified by PVDF (polyvinylidene fluoride) and an electrode provided on each end of the piezoelectric body.

When the electrodes of each of the oscillators are supplied with a pulsed voltage or a continuous-wave voltage, the piezoelectric body expands and contracts to cause the oscillator to produce pulsed or continuous ultrasonic waves. These ultrasonic waves are combined to form an ultrasonic beam. Upon reception of propagating ultrasonic waves, the piezoelectric body of each oscillator expands and contracts to produce an electric signal, which is then outputted as an ultrasonic reception signal.

The transmission driver 11 includes, for example, a plurality of pulsers and adjusts the delay amounts of driving signals for the respective transducers 3 based on a transmission delay pattern selected by the transmission controller 12 so that the ultrasonic waves transmitted from the transducers 3 form a broad ultrasonic beam covering an area of a tissue of the subject to be diagnosed and supplies the transducers 3 with adjusted driving signals.

The reception signal connecting section 4 comprises a plurality of switches connecting and disconnecting between the transducers 3 and corresponding input terminals of the multiplexer 5. According to the instruction by the probe controller 15, the reception signal connecting section 4 is turned off during transmission of ultrasonic waves and turned on during reception of ultrasonic waves to connect the transducers 3 to the corresponding input terminals of the multiplexer 5.

The multiplexer 5 is a 2:1 multiplexer having one output terminal c for a pair of input terminals a and b and alternately connects the input terminals a and b to the output terminal c at a predetermined sampling period Ts according to the instruction from the probe controller 15.

Specifically, out of a plurality of channels of reception signals, two channels of reception signals from two transducers 3 adjacent to each other are alternately connected to the respective reception signal processor 6 at a predetermined sampling period Ts via each of the switches of the reception signal connecting section 4 turned on during ultrasonic wave reception.

Under the control by the reception controller 13, each of the reception signal processors 6 subjects the reception signal outputted from the transducers 3 connected via the reception signal connecting section 4 and the multiplexer 5 to quadrature detection or quadrature sampling to produce a complex baseband signal and samples the complex baseband signal to produce reception data containing information on the area of the tissue. The reception signal processors 6 may produce reception data by performing high efficiency coding data compression on the data obtained by sampling the complex baseband signals.

The data storage unit 7 is configured by, for example, a memory and stores at least one frame of reception data produced by the reception signal processors 6.

The phasing adder 8, constituting a beam former in this invention, selects one reception delay pattern from a plurality of previously stored reception delay patterns according to a reception direction set by the controller 15 and, based on the selected reception delay pattern, provides respective delays in a plurality of complex baseband signals represented by the reception data and adds them up thereby to performs beam forming on reception data produced by the reception signal processors 6 and having time differences among them. This beam forming yields baseband signals (sound ray signals) in which the focal points of the ultrasonic echoes are made to converge.

The signal processor 9 corrects attenuation of the sound ray signal produced by the phasing adder 8, the attenuation depending on a distance in accordance with a depth of a position at which ultrasonic waves are reflected, and then converts the sound ray signal into an image signal compatible with an ordinary television signal scanning mode (raster conversion) to produce a B mode image signal, tomographic image information, on a tissue inside the subject.

The wireless communication unit 10 performs carrier modulation based on the B mode image signal produced by the signal processor 9 to produce transmission signals and supplies an antenna with the transmission signals so that the antenna transmits radio waves to achieve transmission of the B mode image signal. The modulation methods that may be employed herein include ASK (Amplitude Shift Keying), PSK (Phase Shift Keying), QPSK (Quadrature Phase Shift Keying), and 16QAM (16 Quadrature Amplitude Modulation).

The wireless communication unit 10 transmits the B mode image signal to the diagnostic apparatus body 2 through wireless communication with the diagnostic apparatus body 2, receives various control signals from the diagnostic apparatus body 2, and outputs the received control signals to the communication controller 14. The communication controller 14 controls the wireless communication unit 10 so that the B mode image signal is transmitted with a transmission wave intensity that is set by the probe controller 15 and outputs various control signals received by the wireless communication unit 10 to the probe controller 15.

The probe controller 15 controls various components in the ultrasound probe 1 according to control signals transmitted from the diagnostic apparatus body 2.

The ultrasound probe 1 has a built-in battery, not shown, which supplies electric power to the circuits inside the ultrasound probe 1.

The ultrasound probe 1 may be an external type probe such as linear scan type, convex scan type, and sector scan type or a probe of, for example, a radial scan type used for an ultrasound endoscope.

On the other hand, the diagnostic apparatus body 2 comprises a wireless communication unit 21, which is connected to an image processor 22. A display controller 23 and an image storage unit 24 are connected to the image processor 22, and a monitor 25 is connected to the display controller 23. Also, a communication controller 26 is connected to the wireless communication unit 21, and an apparatus body controller 27 is connected to the display controller 23 and the communication controller 26. Further, an operating unit 28 for an operator to perform input operations and a storage unit 29 for storing, for example, operation programs are connected to the apparatus body controller 27.

The wireless communication unit 21 transmits various control signals to the ultrasound probe 1 through wireless communication with the ultrasound probe 1. The wireless communication unit 21 demodulates a signal received through an antenna to output a B mode image signal.

The communication controller 26 controls the wireless communication unit 21 so that various control signals are transmitted with a transmission radio wave intensity that is set by the apparatus body controller 27.

The image processor 22 performs various processings required including gradation processing on the B mode image signal inputted from the communication controller 26 and outputs the B mode image signal to the display controller 23 or stores the B mode image signal in the image storage unit 24.

The display controller 23 causes the monitor 25 to display an ultrasound diagnostic image according to the B mode image signal processed by the image processor 22. The monitor 25 includes a display device such as an LCD, for example, and displays an ultrasound diagnostic image under the control of the display controller 23.

In such diagnostic apparatus body 2, the image processor 22, the display controller 23, the communication controller 26, and the apparatus body controller 27 are constituted by a CPU and operation programs for causing the CPU to perform various kinds of processing, but they may be constituted by digital circuits. The aforementioned operation programs are stored in the storage unit 29. The storage unit 29 may be formed by a recording medium such as a hard disk, a flexible disk, an MO, an MT, a RAM, a CD-ROM, a DVD-ROM, a SD card, a CF card, a USB memory, or a server.

Next, the operation of Embodiment 1 will be described.

Upon starting of ultrasound diagnosis, the probe controller 15 first turns off the switches of the reception signal connecting section 4, and in this state, the plurality of transducers 3 constituting the transducer array transmit ultrasonic waves according to the driving signals supplied from the transmission driver 11 of the ultrasound probe 1.

Upon termination of transmission of ultrasonic waves from the transducers 3, the probe controller 15 immediately turns on the switches of the reception signal connecting section 4, connecting the transducers 3 to the corresponding input terminals of the multiplexer 5. In this time, the multiplexer 5 alternately connects the input terminals a and b to one output terminal c at the predetermined sampling period Ts according to the instruction by the probe controller 15. Accordingly, a reception signal from one transducer 3 whose channel is connected to the input terminal a of the multiplexer 5 is supplied to one reception signal processor 6 to produce reception data A, thereafter a reception signal from a neighboring transducer 3 whose channel is connected to the input terminal b of the multiplexer 5 is supplied to the reception signal processor 6 to produce reception data B. That is, the reception data A and the reception data B are alternately produced by each of the reception signal processors 6 and stored in the data storage unit 7 in sequence.

Figure 2:
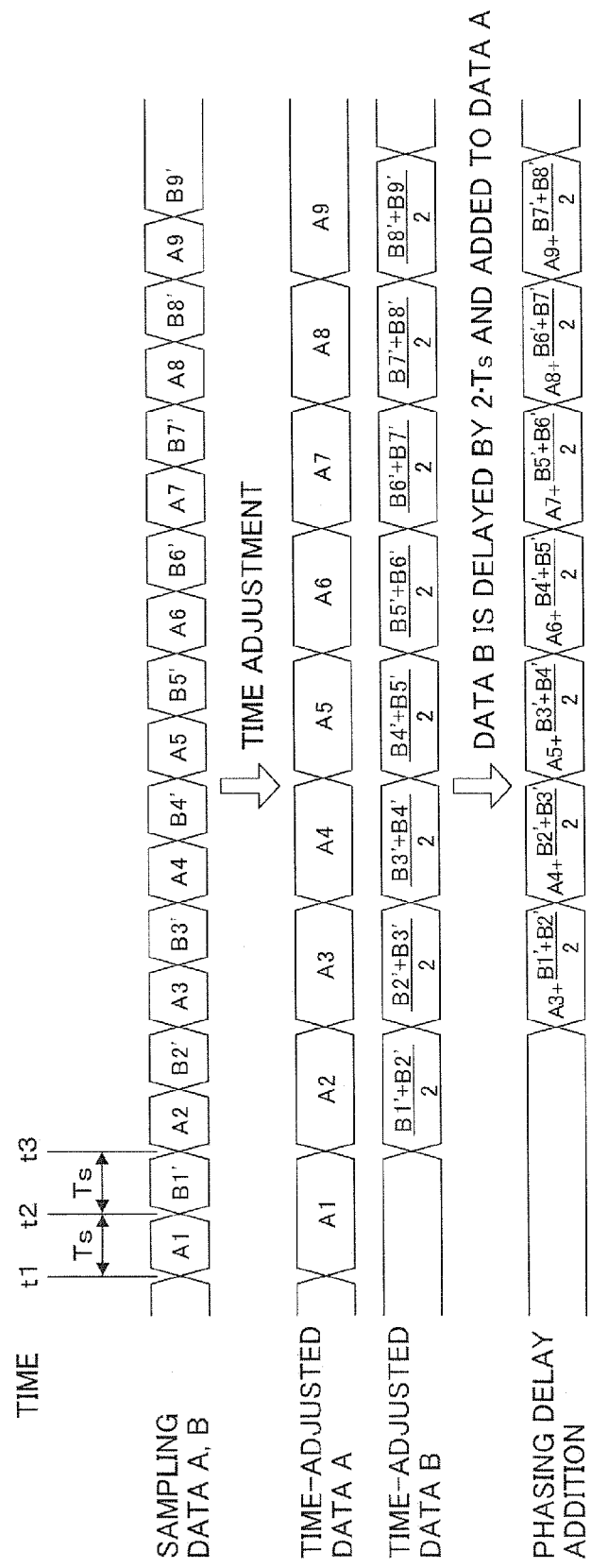
FIG. 2 is a timing chart illustrating how signal processing is performed in Embodiment 1.

As illustrated in FIG. 2, for example, a reception signal from one transducer 3 whose channel is connected to the input terminal a of the multiplexer 5 is sampled by one reception signal processor 6 at time t1 to produce first reception data A1. At time t2 after a given sampling period Ts has elapsed from time t1, a reception signal from a neighboring transducer 3 whose channel is connected to the input terminal b of the multiplexer 5 is sampled by the reception signal processor 6 to produce first reception data B1'. Similarly, at time t3 after the given sampling period Ts has elapsed from time t2, a reception signal from the one transducer 3 whose channel is connected to the input terminal a of the multiplexer 5 is sampled by the reception signal processor 6 to produce second reception data A2.

Thus, one reception signal processor 6 alternately processes the reception signals from two channels of transducers 3.

The reception data based on the reception signals from the neighboring transducer 3 whose channel is connected to the input terminal b of the multiplexer 5 are labeled with "'" attached such as "B1'" for the sake of convenience to show that they are data sampled at a timing the given sampling period Ts later than the reception data based on the reception signals from the one transducer 3 whose channel is connected to the input terminal a.

Thus, the reception data A1, B1', A2, B2', A3, B3', . . . produced at intervals of the given sampling period Ts are stored in the data storage unit 7.

The phasing adder 8 first makes time adjustment between the reception data A1, A2, A3, . . . based on the reception signals from the one transducer 3 whose channel is connected to the input terminal a of the multiplexer 5 and the reception data B1', B2', B3' . . . based on the reception signals from the neighboring transducer 3 whose channel is connected to the input terminal b of the multiplexer 5 to eliminate time difference between the reception data A1, A2, A3, . . . and the reception data B1', B2', B3', . . . .

For example, out of the two channels connected to the input terminals a and b of the multiplexer 5, let the channel connected to the input terminal a be a base channel. Then, because the reception data A1, A2, A3, . . . for this base channel are sampled once every two periods (2·Ts), these data are handled as data for two periods (2·Ts) to form the time-adjusted reception data A.

On the other hand, as to the reception data B in the other channel than the base channel, i.e., the channel connected to the input terminal b of the multiplexer 5, the reception data B1', for example, is data obtained by sampling at a timing earlier than the reception data A2 of the base channel by one sampling period Ts, and the reception data B2' is data obtained by sampling at a timing later than the reception data A2 of the base channel by one sampling period Ts. Therefore, a temporal 2-point interpolated value (B1'+B2')/2 between the reception data B1' and B2' is calculated and thus calculated value is regarded as data for 2 periods (2·Ts) sampled at the same timing as the reception data A2. Similarly, 2-point interpolated values (B2'+B3')/2, (B3'+B4')/2, (B4'+B5')/2, . . . , which can be regarded as data sampled at the same timing as the reception data A3, A4, A5, . . . , respectively, are calculated to obtain time-adjusted reception data B.

Subsequently, the phasing adder 8 adds the reception data A and the reception data B with making a delay therebetween corresponding to the reception direction set by the probe controller 15. FIG. 2 illustrates results of, for example, the reception data B being delayed by 2 periods (2·Ts) and added to the reception data A.

The reception signals from two transducers 3 neighboring to each other are likewise alternately processed by each of the reception signal processors 6, until all the reception signals from the transducers 3 are processed, whereupon the phasing adder 8 performs beam forming to produce sound ray signals.

Then, based on the sound ray signals produced by the phasing adder 8, a B-mode image signal is produced by the signal processor 9 and wirelessly transmitted via the wireless communication unit 10 to the diagnostic apparatus body 2. The B mode image signal received by the wireless communication unit 21 is suffered with image processing including gradation processing by the image processor 22, and based on this processed B-mode image signal, an ultrasound diagnostic image is displayed on the monitor 25 by the display controller 23.

Because Embodiment 1 has a configuration such that the reception signals from two transducers 3 are processed by one reception signal processor 6 using the 2:1 multiplexer 5, in comparison with a number of channels of transducers 3, only half a number of reception signal processors 6 need be mounted. Therefore, high-quality images can be obtained while greatly saving on power consumption.

The sampling period Ts may be one that is selected as appropriate. However, because the reception signals from two transducers 3 are processed by one reception signal processor 6, the multiplexer 5 needs to be operated at twice the frequency of the data formed by the phasing addition. For example, in order to obtain data formed by the phasing addition at a frequency of 40 MHz, the multiplexer 5 may be operated at a frequency of 80 MHz and therefore the sampling period Ts may be 1.25 ns.

In place of the 2:1 multiplexer 5, an N:1 (N≥3) multiplexer may be used to sequentially select one channel of reception signal in every N number of channels of reception signals, so that one reception signal processor may sequentially processes an N number of channels of reception signals to produce reception data. In this case, out of the reception signals of the N number of channels, the reception signals of the (N−1) number of channels other than the base channel may be temporally interpolated to make time adjustment.

Embodiment 2

Although in Embodiment 1, the 2-point interpolation is performed on only the reception data B for time adjustment among the reception data A and the reception data B produced by the respective reception signal processors 6, the time adjustment may be made by performing the 2-point interpolation on both channels of reception data, the reception data A and B.

Figure 3:
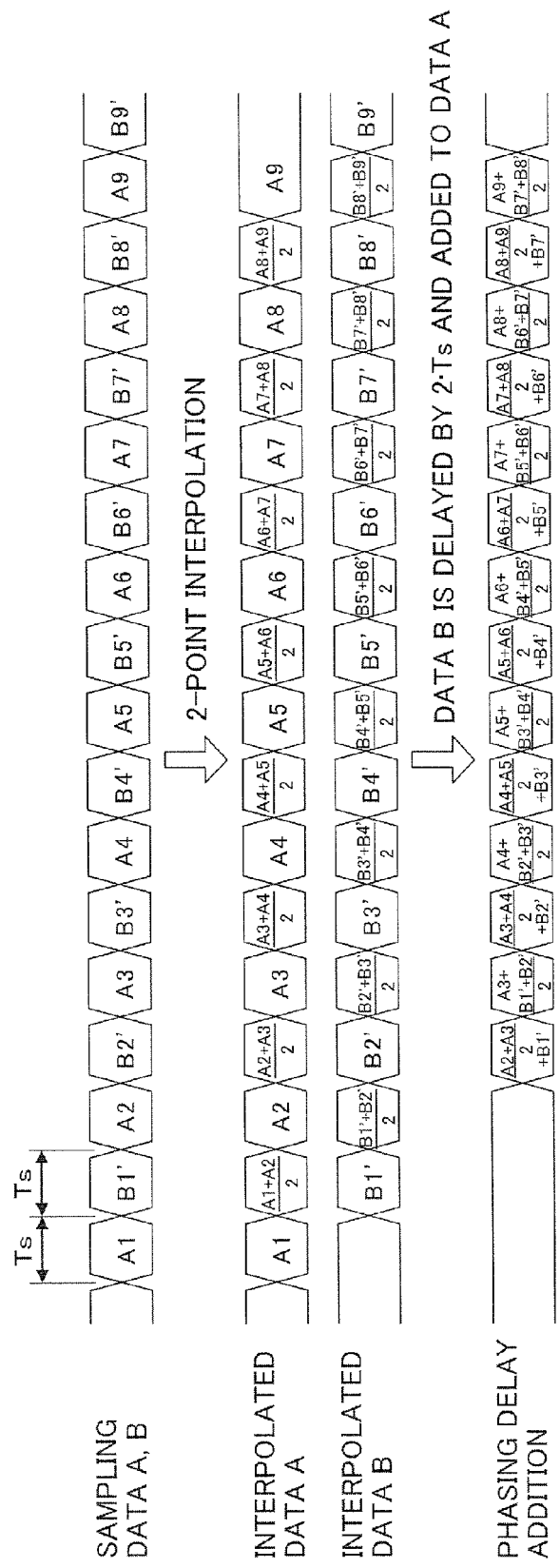
FIG. 3 is a timing chart illustrating how signal processing is performed in Embodiment 2.

As illustrated in FIG. 3, because the reception data A1, A2, A3, . . . are sampled once in every two periods (2·Ts), the reception data A for every sampling period Ts is formed by sequentially performing the 2-point interpolation on the reception data A1, A2, A3, . . . , and, similarly, the reception data B for every sampling period Ts is formed by sequentially performing the 2-point interpolation on the reception data B1', B2', B3', . . . sampled once in every two periods (2·Ts).

Subsequently, the reception data A and the reception data B may be added with making a delay therebetween corresponding to the reception direction set by the probe controller 15. FIG. 3 illustrates results of, for example, the reception data B being delayed by 2 periods (2·Ts) and added to the reception data A.

The above process forms the reception data A and B for every sampling period Ts, and therefore enables reduction in the number of the reception signal processors 6 required, making it possible to obtain images having a still higher image quality while saving on power consumption.

Also according to Embodiment 2, an N:1 (N≥3) multiplexer may be used in place of the 2:1 multiplexer 5 to sequentially select one channel of reception signal in every N number of channels of reception signals, so that one reception signal processor sequentially processes an N number of channels of reception signals to produce reception data. In this case, the time adjustment may be made by temporally interpolating all the N number of channels of reception signals.

Embodiment 3

Figure 4:
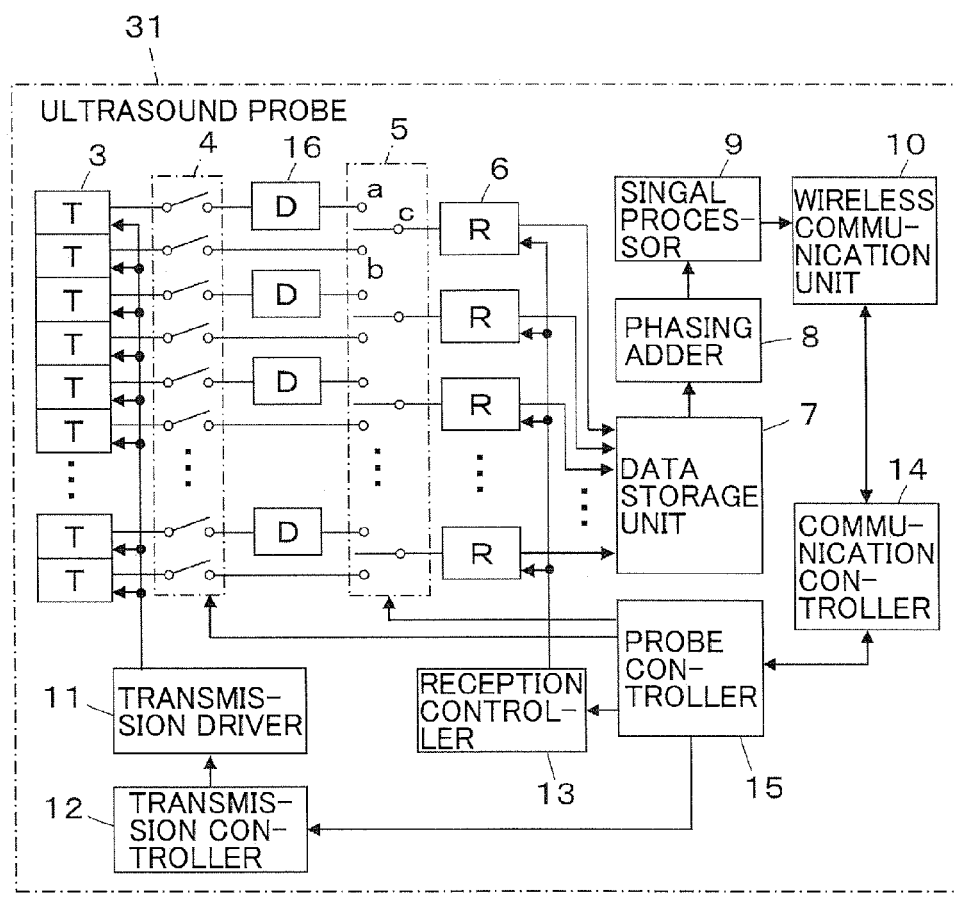
FIG. 4 is a block diagram illustrating a configuration of an ultrasound probe used in an ultrasound diagnostic apparatus according to Embodiment 3.

FIG. 4 illustrates the internal structure of an ultrasound probe 31 used in an ultrasound diagnostic apparatus according to Embodiment 3. As compared with the ultrasound probe 1 illustrated in FIG. 1, the ultrasound probe 31 has a delay circuit 16 inserted between each input terminal a of pairs of terminals a and b of the multiplexer 5 and the corresponding switch of the reception signal connecting section 4. The other components are the same as those of the ultrasound probe 1 according to Embodiment 1.

The delay circuits 16 have a delay time Td of the same length as the sampling period Ts and delay the reception signals from the transducers 3 whose channels are connected to the input terminals a of the multiplexer 5 by the delay time Td with respect to the reception signals from the transducers 3 whose channels are connected to the input terminals b.

According to Embodiment 3, out of the two channels connected to the input terminals a and b of the multiplexer 5, the channel connected to the input terminal b is the base channel, and the reception signal of the other channel than the base channel, i.e., the channel connected to the input terminal a of the multiplexer 5 is delayed by the delay time Td with respect to the reception signal of the base channel.

The multiplexer 5 so operates that the reception data B in the base channel is sampled with a delay corresponding to the sampling period Ts with respect to the reception data A in the other channel than the base channel. Therefore, the reception data A and B that are the same as those sampled at the same timing with respect to each other's channel can be obtained by delaying the reception signal of the other channel than the base channel by the delay time Td having the same length as the sampling period Ts through the corresponding delay circuit 16.

Thus, as illustrated in FIG. 5, the phasing adder 8 makes time adjustment such that the reception data A and B are each for 2 periods (2·Ts) and have the same timing as each other, subsequently adds the reception data A and the reception data B with making a delay therebetween corresponding to the reception direction set by the probe controller 15. FIG. 5 illustrates results of, for example, the reception data B being delayed by 2 periods (2·Ts) and added to the reception data A.

The above process reduces the number of the reception signal processors 6 required, thus making it possible to obtain images having a still higher image quality while saving on power consumption without conducting the interpolation process as required in Embodiments 1 and 2.

Also in Embodiment 3, an N:1 (N≥3) multiplexer may be used in place of the 2:1 multiplexer 5 to sequentially select one channel of reception signal in every N number of channels of reception signals, so that one reception signal processor sequentially processes an N number of channels of reception signals to produce reception data. In this case, out of the reception signals of the N number of channels, the reception signals of the (N−1) number of channels other than the base channel may be each delayed by delay times corresponding to their respective channels to eliminate the time difference among the reception signals.

Although the ultrasound probe 1 or 31 and the diagnostic apparatus body 2 are connected to each other by wireless communication in Embodiments 1 to 3, the invention is not limited thereto. The ultrasound probe 1 or 31 may be connected to the diagnostic apparatus body 2 via a connection cable. Such configuration obviates the necessity of providing the wireless communication unit 10 and the communication controller 14 of the ultrasound probe 1 or 31, the wireless communication unit 21 and the communication controller 26 of the diagnostic apparatus body 2, and the like.

What is claimed is:

1. An ultrasound diagnostic apparatus comprising:
    a transducer array that includes a plurality of ultrasound transducers and transmits ultrasonic beams to a subject and receiving ultrasonic echoes from the subject;
    a transmission driver that supplies driving signals to the plurality of ultrasound transducers to transmit ultrasonic beams to the subject from the transducer array;
    a multiplexer that includes a plurality of input terminals corresponding to the plurality of ultrasound transducers and sequentially selects one channel of reception signal at a predetermined sampling period Ts in every N number of channels of reception signals out of a plurality of channels of reception signals outputted from the transducer array which has received receiving ultrasonic echoes from the subject;
    a reception signal connecting section that comprises a plurality of switches connecting and disconnecting between the plurality of ultrasound transducers of the transducer array and the plurality of input terminals of the multiplexer;
    a controller that controls the transmission driver, the multiplexer and the reception signal connecting section so as to turn off the plurality of switches of the reception signal connecting section to transmit ultrasonic beams from the transducer array according to the driving signals supplied from the transmission driver and to thereafter turn on the plurality of switches of the reception signal connecting section to sequentially select one channel of reception signal in every N number of channels of reception signals by the multiplexer;
    a plurality of reception signal processors that sequentially sample an N number of channels of reception signals selected by the multiplexer at the predetermined sampling period Is to produce an N number of channels of reception data, reception data of each channel being sampled once every N sampling periods;
    a beam former that interpolates data for each channel, performs phasing delay addition of the data of each channel to form time adjusted data in which time differences between the plurality of channels are eliminated, and performs beam forming on the time adjusted data to produce sound ray signals, wherein the interpolation is done for each sampling period Ts where a channel was not directly sampled; and
    an image producing unit that produces an ultrasound image based on the sound ray signals produced by the beam former.

2. The ultrasound diagnostic apparatus according to claim 1, wherein the beam former calculates temporal interpolated values between reception data other than reception data of a base channel out of reception data of an N number of channels sequentially produced by the respective reception signal processors and performing beam forming by using the calculated temporal interpolated values and reception data of the base channel.

3. The ultrasound diagnostic apparatus according to claim 1, wherein the beam former calculates temporal interpolated values between all reception data of an N number of channels sequentially produced by the respective reception signal processors and performing beam forming by using the calculated temporal interpolated values.

4. The ultrasound diagnostic apparatus according to claim 1, wherein the multiplexer is a 2:1 multiplexer.

5. The ultrasound diagnostic apparatus according to claim 1, wherein the multiplexer is a N:1 multiplexer with N≥3.

6. The ultrasound diagnostic apparatus according to claim 1, wherein the reception data includes reception data A1, A2, A3 . . . based on reception signals from a first transducer connected to a first input terminal of the multiplexer, and reception data B1', B2', B3' . . . based on reception signals from a neighboring second transducer connected to a second terminal of the multiplexer.

7. The ultrasound diagnostic apparatus according to claim 6, wherein a temporal 2-point interpolated value (B1'+B2')/2 is calculated for 2 periods sampled at the same timing as reception data A2.

8. The ultrasound diagnostic apparatus according to claim 7, wherein temporal values (B2'+B3')/2, (B3'+B4')/2, (B4'+B5')/2 . . . are sample at the same timing as A3, A4, A5 . . . , respectively to obtain time adjusted reception data.

9. An ultrasound image producing method comprising the steps of:
    transmitting an ultrasonic beam from an transducer array to a subject by supplying driving signals to a plurality of ultrasound transducers included in the transducer array in a state of disconnecting between the plurality of ultrasound transducers of the transducer array and a plurality of input terminals of a multiplexer corresponding to the plurality of ultrasound transducers;
    connecting between the plurality of ultrasound transducers of the transducer array and the plurality of input terminals of a multiplexer to sequentially select one channel of reception signal at a predetermined sampling period Is in every N number of channels of reception signals out of a plurality of channels of reception signals outputted from the transducer array which has received receiving ultrasonic echoes from the subject;
    producing an N number of channels of reception data by sequentially sampling a selected N number of channels of reception signals at the predetermined sampling period Ts, reception data of each channel being sampled once every N sampling periods; interpolating data for each channel, performing phasing delay addition of the data of each channel to form time adjusted data in which time differences between the plurality of channels are eliminated, and performing beam forming on the time adjusted data to produce sound ray signals, wherein the interpolating is done for each sampling period Is where a channel was not directly sampled;
    performing beam forming on the time adjusted data to produce sound ray signals; and
    producing an ultrasound image based on the produced sound ray signals.

10. The ultrasound image producing method according to claim 9, wherein temporal interpolated values between reception data other than reception data of a base channel out of reception data of an N number of channels sequentially produced are calculated and beam forming is performed by using the calculated temporal interpolated values and reception data of the base channel.

11. The ultrasound image producing method according to claim 9, wherein temporal interpolated values between all reception data of an N number of channels sequentially produced are calculated and beam forming is performed by using the calculated temporal interpolated values.

12. The ultrasound image producing method according to claim 9, wherein the sequentially selecting is performed with a 2:1 multiplexer.

13. The ultrasound image producing method according to claim 9, wherein the sequentially selecting is performed with a N:1 multiplexer with N≥3.

14. The ultrasound image producing method according to claim 9, wherein the reception data includes reception data A1, A2, A3 . . . based on reception signals from a first transducer connected to a first input terminal of a multiplexer, and reception data B1', B2', B3' . . . based on reception signals from a neighboring second transducer connected to a second terminal of the multiplexer.

15. The ultrasound image producing method according to claim 14, wherein a temporal 2-point interpolated value (B1'+B2')/2 is calculated for 2 periods sampled at the same timing as reception data A2.

16. The ultrasound image producing method according to claim 15, wherein temporal values (B2'+B3')/2, (B3'+B4')/2, (B4'+B5')/2 . . . are sample at the same timing as A3, A4, A5 . . . , respectively to obtain time adjusted reception data.

* * * * *